United States Patent [19]

Okada

[11] Patent Number: 5,075,490

[45] Date of Patent: Dec. 24, 1991

[54] ASPARTIC ACID DERIVATIVES

[75] Inventor: Yoshio Okada, Akashi, Japan

[73] Assignee: Watanabe Chemical Industries, Ltd., Hiroshima, Japan

[21] Appl. No.: 241,842

[22] Filed: Sep. 8, 1988

[30] Foreign Application Priority Data

Sep. 18, 1987 [JP] Japan .............................. 62-233950

[51] Int. Cl.$^5$ ........................................... C07C 271/34
[52] U.S. Cl. ..................................... 560/27; 560/163; 560/116; 560/125; 560/24; 560/28; 530/330
[58] Field of Search ................. 560/163, 116, 125, 24, 560/27, 28

[56] References Cited

PUBLICATIONS

Okada et al., Chemical Abstracts, vol. 110, entry 76038d (1988).

*Primary Examiner*—John M. Ford
*Attorney, Agent, or Firm*—Heller, Ehrman, White & McAuliffe

[57] ABSTRACT

New compounds N-α-9-fluorenylmethoxycarbonyl-aspartic acid-β-1-adamantyl esters are stable under the basic condition of the normal peptide condensation process and do not form succinimide. Peptides containing aspartic acid can be synthesized with high purity and at high yields by using N-α-9-fluorenylmethoxycarbonyl-aspartic acid-β-1-adamantyl ester.

1 Claim, 1 Drawing Sheet

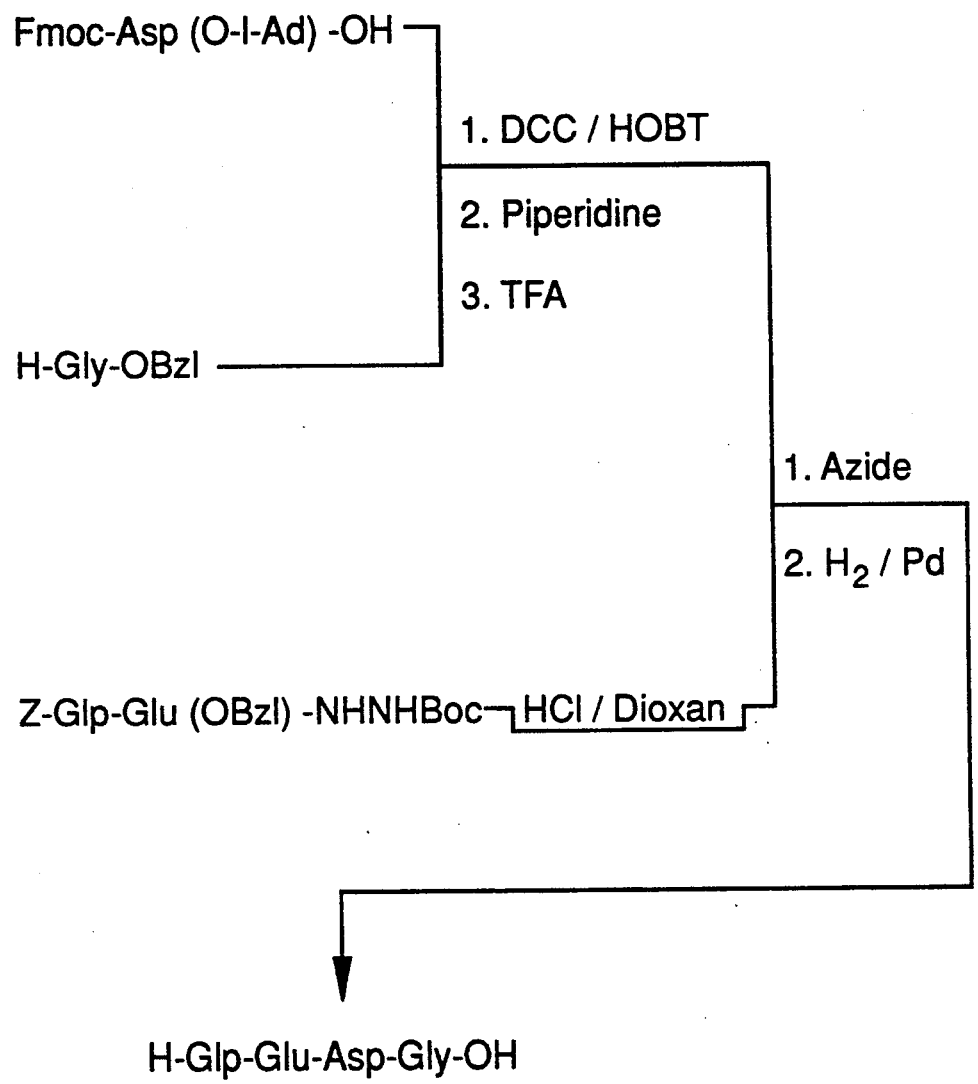
FIG._1

ASPARTIC ACID DERIVATIVES

BACKGROUND OF THE INVENTION

This invention relates to aspartic acid derivatives and a method of peptide synthesis.

With recent developments in the method of analyzing extremely small quantities of components in living bodies, many physiologically active peptides have been discovered which are useful medically or as medicines. Since large quantities of these peptides are required for medical research and as medicines, it is important to develop a method of organic synthesis whereby they can be supplied economically and in large quantities.

In the meantime, instead of the conventional Boc method (B. Ridge, "Amino-Acids Peptides And Proteins", The Chemical Society, Vol. 6, p. 302 (1975)) whereby t-butoxycarbonyl (referred to as Boc) group is used for the protection of α-amino group and an expensive apparatus is used for the final deprotection with hydrogen fluoride, the Fmoc method (Carpino, et al., J. Am. Chem. Soc., Vol. 92, pp. 5748-5749 (1970) and Bodanszki, et al., J. Org. Chem., Vol. 45, pp. 72-76 (1980)) of using 9-fluorenylmethoxycarbonyl (referred to as Fmoc), which allows deprotection under a mildly basic condition, for the protection of α-amino group and trifluoroacetic acid which is a mild acid, for the final deprotection whereby peptides can be synthesized in a simple manner is coming to be frequently used. The present inventors have completed the present invention as a result of diligent studies by observing that, although the Fmoc method is an excellent method of synthesis, it can be applied only to a limited extent to the synthesis of peptides containing aspartic acid because of its deprotection method under a basic condition.

It has been known that the synthesis of aspartyl peptides is accompanied by a succinimide-forming side reaction whether the Boc method or the Fmoc method is used. Formation of succinimide is significant if the peptide contains an aspartyl-glycine or aspartyl-serine linkage and is particularly noteworthy under a basic condition. Although this is convenient for the Fmoc method according to which deprotection is carried out under a basic condition, it is not so for the synthesis of peptides containing aspartic acid. By either method, furthermore, it has been difficult to synthesize such peptides with high purity and at a high yield (Battersby, et al., J. Chem. Soc., pp 259-269 (1955) and Hanson, et al., ibid., 836-842 (1964)).

SUMMARY OF THE INVENTION

It is therefore an object of the present invention to eliminate the difficulties of the conventional method of synthesizing peptides containing aspartic acid.

It is another object of the present invention to provide aspartic acid derivatives which are stable and do not form succinimide under the basic conditions of the ordinary peptide condensation process.

The above and other objects are achieved by the present invention which relates to N-α-9-fluorenylmethoxycarbonyl-aspartic acid-β-1-adamantyl ester and a method of peptide synthesis by using the same.

BRIEF DESCRIPTION OF THE DRAWING

The accompanying drawing, which is incorporated in and forms a part of the specification, is a flowchart of processes for peptide synthesis embodying the present invention and, together with the following detailed description, serves to explain the principles of the invention.

DETAILED DESCRIPTION OF THE INVENTION

N-α-9-fluorenylmethoxycarbonyl-aspartic acid-β-1-adamantyl ester of this invention is a new compound. Since this compound is stable and does not form succinimide under the basic condition for the normal peptide condensation process, it can be used for the synthesis of peptides containing aspartic acid with high purity and at a high yield. In addition to the ordinary peptide synthesis, the compound of this invention can also be used advantageously for the synthesis of peptides by the Fmoc method.

N-α-9-fluorenylmethoxycarbonyl-aspartic acid-β-1-adamantyl ester of the present invention can be produced by reacting 9-fluorenylmethoxycarbonyl-N-hydroxysuccinimide ester with aspartic acid-β-1-adamantyl ester or by using 1-10, or preferably 1-5 equivalents of 9-fluorenylmethoxycarbonyl-N-hydroxysuccinimide ester with 1 equivalent of aspartic acid-β-1-adamantyl ester. For the introduction of this Fmoc group, use may be made of N-hydroxyphthalylimide ester, N-hydroxy-5-norbornen-2,3-dicarboxyimide ester, 1-hydroxybenzotriazole ester, paranitrophenyl ester, 4,6-dimethoxy-1,3,5-triazin-2-thioester, pentachlorophenyl ester, 1,3,5-trichlorophenyl ester, pentafluorophenyl ester, azide, chloride, bromide and fluoride besides N-hydroxysuccinimide ester. Normally, it is preferred that the reaction take place in the presence of a base such as about 0.01-5 equivalents and preferably about 0.5-5 equivalents of triethylamine, N-methylmorpholine, N,N-dimethylaniline, N,N-diethylaniline, N,N-diisopropylethylamine, pyridine, piperidine, pyridazine, pyrazine, pyrimidine, sodium hydroxide, potassium hydroxide, lithium hydroxide, magnesium oxide, sodium carbonate, potassium carbonate, sodium hydrogencarbonate and potassium hydrogencarbonate for 1 equivalent of 9-fluorenylmethoxycarbonyl-N-hydroxysuccinimide ester. It is generally preferred that this reaction take place in an appropriate solvent such as water, acetone, dioxane, dimethylformamide, tetrahydrofuran, acetonitrile, dimethyl sulfoxide or a mixture thereof and at temperature −20° C.-60° C. and preferably −5° C.-40° C. Another method of obtaining N-α-9-fluorenylmethoxycarbonyl-aspartic acid-α-1-adamantyl ester is to introduce 1-adamantanol to N-α-9-fluorenylmethoxycarbonyl-aspartic acid-α-benzyl ester by the method of Tam, et al. (disclosed in Tetrahedron Letters, Vol. 42, pp. 4033-4036 (1979)) to produce N-α-9-fluorenylmethoxycarbonyl-aspartic acid-α-benzyl ester-β-1-adamantyl ester and then to remove α-benzyl ester therefrom by a method such as catalytic reduction. N-α-9-fluorenylmethoxycarbonyl-aspartic acid-β-1-adamantyl ester thus obtained is used for peptide condensation by a usual method disclosed, for example, in "The Peptides" by E. Schroeder and K. Luebke (Academic Press, Inc., New York (1965)), "The Peptides" Vols. 1 and 2 by E. Gross and J. Meinhofer (Academic Press, Inc., New York (1979 and 1980)) and "Lectures On Experiments In Biochemistry 1, Protein Chemistry IV, Peptide Synthesis" by H. Yajima (Tokyo Kagaku Dojin (1977)) such as the azide method, the chloride method, the acid anhydride method, the mixed acid anhydride method, the DCC method, the active ester method, the EEDQ method, a method by the Woodward reagent K, the carbonyldiimidazole method, the oxidation-reduction method and the DCC-HOBT method. Next, the Fmoc group is removed after the peptide condensation by using a base such as a potassium hydroxide, sodium hydroxide, lithium hydroxide, magnesium oxide, hydrogencarbonate, potassium hydrogencarbonate, triethylamine, diethylamine, diisopropylethylamine, N-methylmorpholine, pyridine, piperidine, pyridazine, pyrazine and pyrimidine at a concentration of 1–100% with or without a solvent such as water, acetone, dioxane, tetrahydrofuran, dimethylformamide, dimethylacetoamide, hexamethylene phosphoric triamide, N-methylpyrrolidone, acetonitrile, dimethyl sulfoxide or a mixture thereof. The base has only to be added to the extent sufficient to remove the protecting groups. More in detail, $1-10^5$ equivalents, or preferably $1-10^3$ equivalents should be added to one equivalent of the Fmoc group. Temperature should be $-20°$ C.$-100°$ C. or preferably $-10°$ C.$-60°$ C. The 1-adamantyl group which is the protecting group of the aspartic acid-$\beta$-carboxyl group, is removed with an acid by any known acid processing method such as the anhydrous hydrogen fluoride method and the methane sulfonic acid method. Alternatively, a mild acid such as trifluoroacetic acid may be used for this purpose at a rate sufficient to serve as a solvent and to remove the protecting groups, that is, $1-10^5$ equivalents or preferably $1-10^3$ equivalents for one equivalent of 1-adamantyl group at a temperature of $-20°$ C.$-100°$ C. or preferably about $-10°$ C.$-60°$ C.

The method according to the present invention can be applied to the synthesis of any peptides containing aspartic acid. As will be shown below more in detail, for example, physiologically active insulin-releasing tetrapeptides (disclosed by Reichelt, et al., Biochem. Biophys. Res. Commun., Vol. 122, pp. 103–110 (1984)) can be synthesized advantageously. Other examples include human chorionic gonadotropin, human $\beta$-lipotropic hormone, human GIP, urogastrone, parathyroid hormone, MSH, growth hormone, prolactin, thyrotropic hormone (thyrotropin), gastrin, galanin, calcitonin and their active pieces.

The calcitonin group of the N-$\beta$-9-fluorenylmethoxycarbonyl-aspartic acid-$\beta$-1-adamantyl ester used in the method of the present invention has a superior selective characteristic compared to the conventional $\beta$-carboxyl group of aspartic acid in that it is fairly stable under a basic condition but can be removed extremely easily by the deprotection method under an acidic condition prepared with trifluoroacetic acid. Thus, it can be used extremely advantageously in the Fmoc method whereby the peptide chain is extended by removing the $\alpha$-amino protecting groups under a basic condition.

The $\beta$-1-adamantyl group of N-$\alpha$-9-fluorenylmethoxycarbonyl-aspartic acid has another remarkable characteristic that it is fairly resistive against hycrochloric acid but it can be removed by trifluoroacetic acid easily under the same acidic condition. This is a new characteristic not found in a conventional acid deprotection group such as the Boc group. This subtle difference in characteristics will probably be utilized in the future in applications to the synthesis of more complicated peptides for which use of polyfunctional groups may be required. In other words, N-$\alpha$-9-fluorenylmethoxycarbonyl-aspartic acid-$\beta$-1-adamantyl ester of the present invention is a compound rich in future potentialities.

In what follows, the present invention will be explained more in detail by way of examples but they are not intended to limit the scope of the present invention. The processes of peptide synthesis according to the present invention are summarized in the accompanying drawing. Abbreviations based on the IUPAC-IUB Commission On Biological Nomenclature as well as those commonly accepted by persons in the art will be used in these examples. Some of these abbreviations are summarized in Table 1. Angles of rotation presented below were all measured by using the sodium D-line.

TABLE 1

| | |
|---|---|
| Glp: | pyroglutamic acid |
| Glu: | glutamic acid |
| Glu(OBzl): | $\gamma$-benzyl-glutamic acid |
| Asp: | aspartic acid |
| Gly: | glycine |
| Z: | carbobenzoxy |
| Boc: | t-butoxycarbonyl |
| O-1-Ad: | 1-adamantyl ester |
| OBzl: | benzyl ester |
| DCC: | N,N'-dicyclohexylcarbodiimide |
| TFA: | trifluoroacetic acid |
| MSA: | methanesulfonic acid |
| $NH_2NH_2$—$H_2O$: | hydrazin hydrate |
| $Et_3N$: | triethylamine |
| HOBT: | 1-hydroxybenzotriazole |
| DMAP: | 4-dimethylaminopyridine |
| OSu: | N-hydroxysuccinimide ester |

Unless specified otherwise, L-configuration is implied for amino acids (except Gly).

REFERENCE EXAMPLE 1

1 Synthesis of N-$\alpha$-carbobenzyoxy-aspartic acid-$\beta$-1-adamantyl ester-$\alpha$-benzyl ester (abbreviated as Z-Asp(O-1-Ad)-OBzl)

Dissolved in 50 ml of methylene chloride was 2.00 g (0.0056 mole) of N-$\alpha$-carbobenzoxy-aspartic acid-$\alpha$-benzyl ester (abbreviated as Z-Asp-OBzl) and 0.95 g (0.0062 mole) of 1-adamantanol was added to the mixture which was cooled with ice. To this mixture were added 0.171 g (0.0014 mole of DMAP and 1.27 g (0.0062 mole) of DCC and it was stored overnight. The generated DCC-urea was removed and methylene chloride was removed by evaporation. The residue was extracted with ethyl acetate. The ethyl acetate layer was washed with water and after it was dried, ethyl acetate was removed by evaporation at a reduced pressure. Petroleum benzine was added to the residue and the generated crystals were collected by filtering. Ethanol was used for recrystallization. The test results were as follows:

Yield: 1.38 g (50.2%).
Melting Point: 94°–95° C.
Angle of Rotation: $[\alpha]^{23}$ +8.6° (C=1.0 in chloroform).
Thin-Film Chromotography (TLC): $Rf_1$ (benzene) = 0.24, $Rf_2$ (chloroform: ether = 4:1) = 0.92.
Elementary Analysis (as $C_{29}H_{33}O_6N$).
Calculated Values: C = 70.9; H = 6.77; N = 2.85.
Experimental Values: C = 70.9; H = 6.80; N = 3.09.

(2) Synthesis of aspartic acid-$\beta$-1-adamantyl ester (abbreviated as H-Aso(O-1-Ad)-OH)

Suspended in 40 ml of methanol was 1.20 g (2.44 mmole) of Z-Asp(O-1-Ad)-OBzl and a solution was obtained by a known method of catalytic reduction with palladium black as catalyst. The catalyst was filtered away and the filtrate was concentrated under a reduced pressure. The generated crystals were collected by filtering. The test results were as follows:

Yield: 0.60 g (89%).
Melting Point: 240°–241° C. (decomposition).
Angle of Rotation: $[\alpha]^{23}$ -15.2° (C=0.6, methanol).
TLC: $Rf_3$ (n-butanol:acetic acid:pyridine:water = 4:1:1:2) = 0.57 and $Rf_4$ [ upper layer of (n-butanol:acetic acid:water = 4:1:5)] = 0.40.
Elementary Analysis (as $C_{14}H_{21}O_4N - 1/2H_2O$).
Calculated Values: C = 0.85; H = 8.03; N = 5.07.
Experimental Values: C = 60.38; H = 8.11; N = 5.00.

MODEL EXPERIMENT 1

Synthesis of N-α-9-fluorenylmethoxycarbonyl-aspartic acid-β-1-adamantyl ester (abbreviated as Fmoc-Aso(O-1-Ad)-OH) from H-Aso(O-1-Ad)-OH.

Added to 100 mg (0.36 mmole) of H-Asp(O-1-Ad)-OH was 1 ml (0.36 mmole) of 5% water solution of triethylamine and 1 ml of acetonitrile solution with 121 mg (0.36 mmole) of Fmoc-OSu was added to the mixture. Thereafter, 1 ml (0.36 mole) of 5% water solution of triethylamine was dropped over a period of one hour. After the mixture was stirred for one hour at room temperature, the solvent was removed by evaporation at reduced pressure. The residue was made acidic by adding one N-HCl and extracted with ether. The ether layer was carefully washed with saturated salt water and after it was dried, ether was removed by evaporation at reduced pressure. A precipitate was obtained by adding n-hexane to the residue. White powder was obtained by reprecipitation with ether and n-hexane. The test results were as follows:

Yield: 120 mg (68.1%).
Angle of Rotation: $[\alpha]^{30}$ +36.6° (C=0.5, chloroform) $[\alpha]^{30}$ +0.2° (C=1.0, methanol).
TLC: $Rf_5$ (chloroform:methanol:acetic acid = 90:8:2) = 0.49.
Elementary Analysis (as $C_{29}H_{31}O_6N - 1/4H_2O$).
Calculated Values: C = 70.50; H = 6.43; N = 2.84.
Experimental Values: C = 70.51; H = 6.48; N = 2.86.
Infrared Absorption Spectrum (KBr): 2912, 1730 $cm^{-1}$.

REFERENCE EXAMPLE 2

Synthesis of N-α-9-fluorenylmethoxycarbonyl-aspartic acid-α-benzyl ester (referred as Fmoc-Aso-OBzl)

Dissolved in 50 ml of tetrahyduran was 3.55 g (0.010 mole) of N-α-9-fluorenylmethoxycarbonyl-aspartic acid (referred as Fmoc-Asp-OH) and DCC was added to the mixture as it was cooled with ice. After one hour, it was gradually returned to room temperature and it was stirred continuously for a total of five hours. The generated precipitate of DCC-urea was filtered away and 1.08 g (0.01 mole) of benzyl alcohol was added to the filtrate and it was stirred at room temperature for 24 hours. Insoluble substances were removed by filtration and the filtrate was removed by evaporation. The residue was dissolved in 10 ml of ether and 2.72 g (0.015 mole of dicyclohexylamine was added. After the mixture was stirred for ten minutes, 20 ml of n-hexane was added and the generated precipitate was collected by filtering. The obtained powder was suspended in 40 ml of ethyl acetate and the mixture was stirred after 40 ml of 5% solution of potassium hydrogensulfate was added. The ethyl acetate layer was washed carefully with water and dried and the solvent was removed by evaporation. To the residue, n-hexane was added for crystallization. Ethanol and water were then used for recrystallization. The test results were as follows:

Yield: 2.89 g (65.0%).
Melting Point: 113–115° C.
Angle of Rotation: $[\alpha]^{25}$ +4.0° (C=1.0, methanol).
TLC: $Rf_6$ (chloroform:methanol:water = 200:75:13) = 0.80.
Elementary Analysis (as $C_{26}H_{23}O_6N$):
Calculated Values: C=70.10; H=5.20; N=3.14.
Experimental Values: C=70.34; H=5.27; N=3.21.

MODEL EXAMPLE 2

Another method of synthesis of Fmoc-Asp(O-1-Ad)-OH (from Fmoc-Asp-OBzl)

Dissolved in 50 ml of methylene chloride was 2.00 g (0.0045 mole) of Fmoc-Asp-OBzl and it was cooled with ice after 0.75 g (0.0050 mole) of 1-adamantanol was added. To this were added 0.14 g (0.0011 mole) of DMAP and 1.03 g (0.0050 mole) of DCC and the mixture was stirred at 4° C. overnight. The generated DCC-urea was removed and methyl chloride was removed by evaporation. The residue was extracted with ethyl acetate. After the ethyl acetate layer was washed carefully with water and dried, ethyl acetate was removed by evaporation at reduced pressure and 50 ml of methanol was added to the residue for a known method of catalytic reduction with palladium black as catalyst. The catalyst was removed by filtration and the filtrate was removed by evaporation. The residue was extracted with ether and after the ether layer was washed carefully with water and dried, ether was removed by evaporation at reduced pressure and a precipitate was obtained by adding n-hexane to the precipitate. Ether and n-hexane were used for reprecipitation and white powder was obtained. The test results were as follows:

Yield: 1.26 g (57.2%).
Angle of Rotation: $[\alpha]^{30}$ +36.6° (C=0.5, chloroform).
$[\alpha]^{30}$ +0.2° (C=1.0, methanol).
TLC: $Rf_5$ = 0.49.
Elementary Analysis (as $C_{29}H_{31}O_6N - 1/4H_2O$).
Calculated Values: C=70.50; H=6.43; N=2.84.
Experimental Values: C=70.60; H=6.35; N=2.68.
Infrared Absorption Spectrum (KBr): 2912, 1730 $cm^{-1}$.

TEST EXAMPLE 1

Added to 20 μmole of Fmoc-Asp(O-1-Ad)-OH at room temperature (20° C.) was 2 ml (500 equivalents) of dimethylformamide containing 55% of piperidine (referred as 55% piperidine/DMF). The mixture was stirred and TLC analysis was performed 60 minutes, 120 minutes and 24 hours thereafter. In all analyses, a single spot representing H-Asp(O-1-Ad)-OH of $Rf_3$=0.57 and $Rf_4$ =0.40 was obtained.

REFERENCE EXAMPLE 3

Under each of the following seven conditions, 20 μmole of H-Asp(O-1-Ad)-OH was processed at room temperature (20° C.) for (a) 5 minutes, (b) 60 minutes and (c) 120 minutes and after each processed sample was adjusted to ph2 with 1N-$Na_2CO_3$ and 1N-HCl, water was added to make the volume 5 ml for analysis of amino acid and the amount of generated aspartic acid was measured;

(1) 2 ml (100 equivalents) of 1N-HCl
(2) 0.5 ml (300 equivalents) of PFA
(3) 0.5 ml (400 equivalents) of MSA
(4) 2 ml (100 equivalents) of 1N-Na$_2$CO$_3$
(5) 2 ml (200 equivalents) of 10% NH$_2$NH$_2$-H$_2$O
(6) 2 ml (70 equivalents) of dioxane containing 10% of Et$_3$N (referred as Et$_3$N/Dioxane)
(7) 2 ml (500 equivalents) of 55% Piperidine/DMF
For the sake of comparison,
(8) 2 ml (100 equivalents) of 1N-Na$_2$CO$_3$
was added to 2 μmole of aspartic acid-β-benzyl ester (referred as H-Asp(OBzl)-OH) at room temperature (20° C.) and measurements were made similarly thereof. The test results are shown together in Table 2.

TABLE 2

| Sample | Condition | Yield of aspartic acid (%) after | | |
|---|---|---|---|---|
| | | 5 min | 60 min | 120 min |
| H-Asp(O-1-Ad)-OH | (1) | 0 | 0 | 2 |
| | (2) | 100 | | |
| | (3) | 100 | | |
| | (4) | 0 | 1 | 3 |
| | (5) | 0 | 0 | 0 |
| | (6) | 0 | 0 | 0 |
| | (7) | 0 | 0 | 0 |
| H-Asp(OBzl)-OH | (8) | 5 | 48 | 60 |

Apparatus for amino acid analysis: Model K-101AS produced by Kyowa Seimitsu, Inc.

MODEL EXAMPLE 3

Synthesis of Z-Glp-Glu(OBzl)-Asp-Gly-OBzl

Dissolved in 5 ml of DMF were 1.96 g (4.00 mmole) of Fmoc-Asp(O-1-AD)-OH and 1.48 g (4.40 mmole) of glycinbenzyl ester-p-toluene sulfonate and after 0.44 g (4.4 mmole) of Et$_3$N was added, 0.67 g (4.40 mmole) of HOBT was added and the mixture was cooled with ice. After 0.91 g (4.40 mmole) of DCC was added and the mixture was stirred for one hour, it was stirred overnight at 4° C. and the generated DCC-urea was removed by filtration. The filtrate was removed by evaporation at reduced pressure and after ethyl acetate was added to the residue, the mixture was washed sequentially with 1N-HCl and water and dried and ethyl acetate was removed by evaporation at reduced pressure. After 20 ml of 55% piperidine/DMF was added to the residue at room temperature (20° C.) and the mixture was stirred for one hour, pressure was reduced for hardening. After 10 ml of TFA was added to the residue and the mixture was stirred for one hour at room temperature, TFA was removed by evaporation at reduced pressure. The residue was vacuum-dried overnight over potassium hydroxide, dissolved in 5 ml of DMF, cooled with ice and stirred as TFA-H-Asp-Gly-OBzl/DMF. On the other hand, 1.6 ml (9 mmole) of ice-cooled dioxane solution of 6N-HCl was added to 1.70 g (3 mmole) of Z-Glp-Glu(OBzl)-NHNH-Boc and after the mixture was stirred for 10 minutes while being cooled with ice, 1.6 ml of DMF was added, the mixture was cooled to −20° C., 0.42 ml (3 mmole) of isoamyl nitrite was added, and Et$_3$N was used to adjust the mixture to ph 8. This reactive liquid was added to the earlier prepared TFA-H-Asp-Gly-OBzl/DMF and after 1.40 ml (10 mmole) of Et$_3$N was further added to the mixture, the mixture was stirred overnight at 4° C. The solvent was removed by evaporationat reduced pressure and ethyl acetate was used for extraction. The ethyl acetate layer was washed with 1N-HCl and water, dried and removed by evaporation at reduced pressure and ether was added to the residue to obtain a gel-type solid substance. Ethyl acetate and ether were used for reprecipitation. The test results were as follows:

Yield: 1.01 g (45.2%).
Melting Point: 155-161° C.
Angle of Rotation: $[\alpha]^{23}$ −49.8° (C=0.5, methanol).
TLC: Rf$_5$ = 0.16, Rf$_6$ = 0.88.
Elementary Analysis (as C$_{38}$H$_{40}$N$_4$O$_{12}$).
Calculated Values: C=61.3; H=5.41; N=7.52.
Experimental Values: C=61.2; H=5.47; N=7.63.

MODEL EXAMPLE 4

Synthesis of H-Glo-Glu-Aso-Glv-OH (insulin releasing tetrapeptide)

Dissolved in a mixture of 10 ml of methanol and 6 ml of DMF was 200 g (0.27 mmole) of Z-Glp-Glu(OBzl)-Asp-Gly-OBzl and palladium black was used as catalyst for a known method of catalytic reduction. The catalyst was removed by filtration and the filtrate was concentrated at reduced pressure. Ether was added to the residue to harden it and it was collected by filtration. The test results were as follows:

Yield: 92 mg (79.6%).
Angle of Rotation: $[\alpha]^{23}$ − 42.8° (C=0.5, water).
TLC: (n-butanol:acetic acid:pyridine:water = 4:1:1:2) = 0.21 Rf$_9$ (n-butanol:acetic acid:pyridine:water = 1:1:1:1) = 0.50.
Elementary Analysis (as C$_{16}$H$_{22}$N$_4$O$_{10}$·1/4H$_2$O).
Calculated Values: C=44.2; H=5.22; N=12.9.
Experimental Values: C=44.1; H=5.45; N=13.1.

In summary, since N-α-9-fluorenylmethoxycarbonyl-aspartic acid-β-1-adamantyl esters of the present invention are stable under the basic condition of the normal peptide condensation process and do not form succinimide, peptides containing aspartic acid can be synthesized with high purity and at high yields.

What is claimed is:
1. N-α-9-fluorenylmethoxycarbonyl-aspartic acid-β-1-adamantyl esters.

* * * * *